United States Patent [19]

Britten

[11] Patent Number: 4,593,649

[45] Date of Patent: Jun. 10, 1986

[54] MILK MONITORING APPARATUS AND METHOD

[76] Inventor: Allan M. Britten, 6151 Hannigan Rd., Everson, Wash. 98247

[21] Appl. No.: 580,072

[22] Filed: Feb. 14, 1984

[51] Int. Cl.$^4$ .............................................. A01J 7/00
[52] U.S. Cl. ............................ 119/14.08; 119/14.14; 119/14.15
[58] Field of Search ............... 119/14.08, 14.14, 14.15, 119/14.17

[56] References Cited

U.S. PATENT DOCUMENTS

| | | | |
|---|---|---|---|
| 2,576,808 | 11/1951 | Perkins | 119/14.08 |
| 2,625,643 | 1/1953 | Cordis | 119/14.47 X |
| 3,022,766 | 2/1962 | McKinley | 119/14.14 |
| 3,874,337 | 4/1975 | Umbaugh et al. | 119/14.15 |
| 3,978,460 | 8/1976 | Jaquith | 119/14.14 X |
| 4,064,838 | 12/1977 | Mukarovsky et al. | 119/14.08 |
| 4,325,028 | 4/1982 | Takahashi | 119/14.14 X |

Primary Examiner—Hugh R. Chamblee
Attorney, Agent, or Firm—Hughes & Cassidy

[57] ABSTRACT

An apparatus to monitor temperature of the milk taken from a cow. The apparatus comprises a housing that is mounted to a short tube of a milking claw. It has a tilt switch that causes the device to be operational when in an upright position, and non-operational when the short milk tube is depending downwardly in a non-use condition. The heat transfer coefficients of the apparatus are arranged so as to minimize potential errors in temperature measurement due to wide variation in ambient temperature in a milk parlor.

24 Claims, 10 Drawing Figures

U.S. Patent  Jun. 10, 1986  Sheet 1 of 4  4,593,649
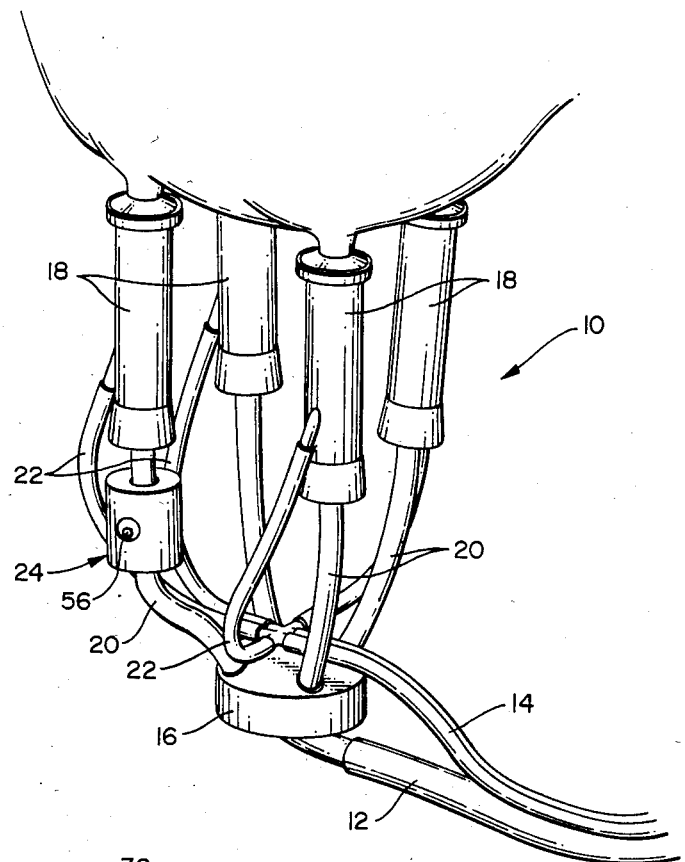
FIG. 1
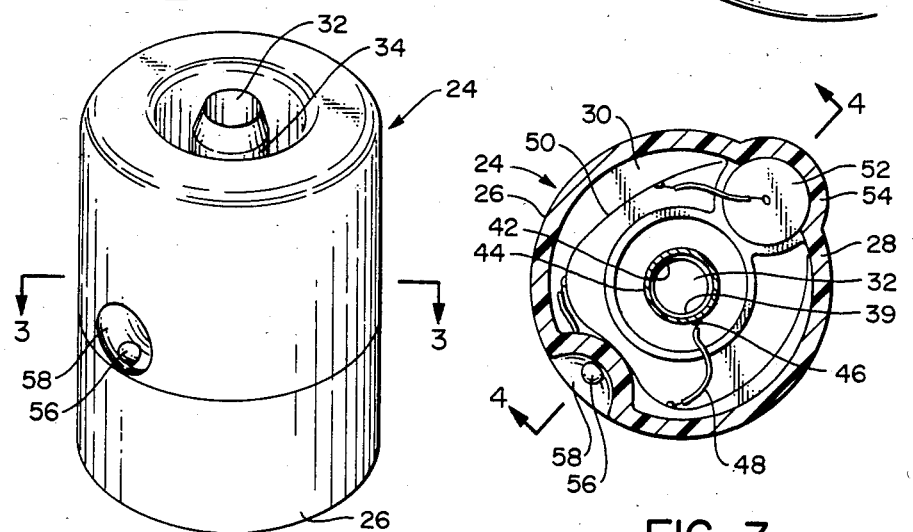
FIG. 2
FIG. 3

4,593,649

MILK MONITORING APPARATUS AND METHOD

BACKGROUND OF THE INVENTION

The present invention relates to a method and apparatus for monitoring temperature, said apparatus and method being particularly adapted to monitor the temperature of milk which is being taken from a cow as a means of determining whether the cow may have a fever.

BACKGROUND ART

It has long been a problem in the dairy industry to detect at an early stage illnesses in the cows who are giving milk. As with humans, a coventional method of detecting illness in a cow is to take the cow's internal temperature. It has also been well known in the dairy industry that the temperature of the milk in the cow's udder is for all practical purposes the same as the internal temperature of the cow. Thus, there has over the years been substantial interest in the possibility of detecting fever in a cow by measuring during the milking operation the temperature of the milk taken from the cow's udder.

The applicant is aware of several milk temperature measuring devices which have either been used or proposed for use commercially. One type that was observed by the applicant had a dial electronic type thermometer with a long probe, and this was alleged to be useful for milking machine monitoring. The unit was battery operated, had a manual on and off switch, and was calibrated manually.

Another unit which the applicant is aware of is identified as "Sure-Temp". This unit was specifically designed for milking machine use. It is provided with a means for insertion of the device into the milk hose some distance downstream from the milking claw. It is battery operated and has a manual on and off switch. To compensate for the problem of the milk cooling after it leaves the cow's udder, there is a manual calibration screw, and the unit is provided with instructions for calibrating.

There is also a unit which is known as the Umbaugh system. This is an automatic take-off unit that uses the cooling of milk as it leaves the cow as a means to detect the end of milk flow. It displays the temperature of the milk on the outside of the take-off by means of an LED display. and it also has a fever alarm, in the form of the LED blinking, when the temperature exceeds a pre-set threshold. This unit addresses the milk cooling problem by providing a manual set screw to bias the thermistor reading as the parlor temperature changes. It appears that it is necessary for the operator to manually reset the bias rather frequently.

A search of the U.S. patents has revealed a number of proposed devices to measure the temperature of the milk leaving the cow or at least perform some sort of temperature measurement related to the milking of the cow.

U.S. Pat. No. 4,064,838, Mukarovsky et al, shows an automatic milking system which has a multiple detector which yields a plurality of output signals to indicate milk flow rate, electrical conductivity of the flowing milk, and also temperature of the flow of milk. It is stated that the multiple detector is associated with an operational amplifier and with a temperature correction circuit to provide a corrected indication of the electrical conductivity of the milk. When the conductivity falls outside a predetermined range, the suction of the teat cups is likewise terminated. Also, the outputs of the delay circuit and the conductivity comparator are coupled to separate portions of an alarm circuit.

U.S. Pat. No. 3,978,460, Jaquith, shows a temperature measuring device where the temperature sensing element is in a weighing device for the milk that comes from the cow. In the introductory portion of the patent, there is a discussion of the problems of measuring the temperature of the milk in the milking device itself because of the introduction of ambient air. Thus, the temperature measuring device is placed at a further downstream location, namely at the weighing device. Further, there is temperature compensation as a function of flow rate.

U.S. Pat. No. 3,022,766, McKinley, shows a temperature measuring device to be used in conjunction with a milking machine where the temperature sensing element is mounted to the manifold (see FIGS. 1 and 2). In FIGS. 3 and 4 of that patent, there is shown another embodiment where the temperature sensing element is inserted through the tube leading from the teat of the cow. More specifically, there is a wire 215 which extends through the tube wall.

U.S. Pat. No. 2,625,643, Cordis, shows a device to heat the cup that is applied to the cow's udder, thus making the cow more comfortable. There is a temperature sensing device to monitor the heat of the cup itself.

Even though the desirability of properly measuring the milk taken from the cow as a means of detecting illness has been known for a long time, and even though there have been various proposals over several decades for accomplishing this measurement of the milk as part of the milking operation itself to the best knowledge of the applicant most of these proposals have not met with commercial success, and also to the best knowledge of the applicant, any that have been used commercially have not had wide acceptance in the dairy industry. However, when one considers the practical problems encountered in the operation of a milk parlor, this is quite understandable. If the temperature sensing device is to be used at the time of the milking operation, it will generally be used in conjunction with, or at least in close association with, the milking apparatus itself. Thus, it would have to be compatible with the existing milking apparatus with regard to structure, how it fits into the system, and ease of operation. If extra manual operations are required (in addition to the actions required simply to accomplish the milking itself), such as turning on switches, calibrating the device, etc., the use of the device may simply be beyond the patience of most milk producers.

Another consideration is the rather stringent sanitation requirements of the dairy industry. The milking equipment must be cleaned at frequent intervals, and normally the milking system is flushed with hot water between each milking. Not only must the temperature sensing device be compatible with the sanitation requirements of the industry, but it should be such as not to interfere with the normal sanitizing operation of the milking equipment itself.

Yet another consideration is the accuracy and reliability of any such temperature measuring device. The temperature in a milking parlor can range normally anywhere from 32° F. to 100° F. and even from day to day there can be substantial fluctuations in the ambient temperature within the milking parlor. Not only would this affect the temperature of the milking apparatus itself, but it would also effect the rate of change at which the temperature of the milk would drop after leaving the cow's udder. A further complicating factor is that in most automated milking machines, ambient air is mixed with the milk that is withdrawn from the cow. For example. in the manifold of the "claw" of the milking apparatus, it is generally filled partly with air and partly with milk. Certain aspects of these temperature problems have been recognized in the prior art. These have affected the location of the temperature sensing device, and have also led to the use of certain compensating devices to allow for temperature variations.

However, the overall effect of variations in ambient temperature relative to the temperature measurement of the milk is a problem with many facets. The applicant's investigation of the various approaches to this overall problem has led the applicant to believe that the unreliability or impracticability of at least some of the prior art approaches has resulted from a lack of full appreciation of how these various heat transfer and temperature considerations interrelate. This will be discussed later in the detailed description of the present invention.

In view of the foregoing, it is a general object of the present invention to provide an apparatus and method for monitoring temperature of a fluid, and more particularly to monitoring temperature of milk which is being extracted from a cow during a milking operation, this being accomplished in a manner that the apparatus itself is rugged, relatively simple and reliable. Further, it is an object to provide such a method and apparatus which is compatible with milking equipment commonly used in dairy milking parlors, and which is compatible in terms of convenient use in a normal milking operation.

SUMMARY OF THE INVENTION

The apparatus of the present invention is adapted to monitor a characteristic of milk that is taken from an animal, this apparatus being adapted to be used in a milking device that extracts the milk from the animal. The apparatus comprises a housing adapted to be mounted relative to said milking device so as to have a first operating position where the housing has a first positional orientation when the milking device is in use, and a second non-operating position where the housing has a second operating position where the housing has a second positional orientation when the milking device is not in use.

It further comprises a sensing means adapted to sense a predetermined condition of a characteristic of the milk and transmit a condition signal related to the condition. There is indicating means to provide an indicating output of the condition of the characteristic of the milk. Further, there is control means to receive the condition signal and to cause said indicating means to provide its output in accordance with the condition signal.

There is a switch means responsive to the positional orientation of the housing to cause the apparatus to be operational when the housing is in its first position and to cause the apparatus to be non-operational when the housing is in its second position.

More specifically, the housing is arranged to be mounted to a tube that receives milk from the animal and transmits the milk to the collector, where said tube has an upright operating position and a non-upright non-operating position. In one arrangement, the housing is provided with a lateral slot to receive the tube so that the housing can be mounted to the tube through the slot. In another arrangement, the housing has first and second tube connecting means adapted to be connected to first and second connecting portions of the tube.

In the preferred form, the apparatus comprises circuit means to give an operational indicating signal in response to the switch means causing the apparatus to become operational. Also, the control means comprises circuit means to give an indicating signal for the indicating means at the time when the sensing means is sensing the condition of the milk. Also, in the preferred form, the control means comprises circuit means to generate an activating signal at a first time and comprising signal storing means to store the activating signal so as to delay transmittal of the same, and to transmit the activating signal to the indicating means at a subsequent time. More specifically, the storage means is responsive to the switch means being activated by the housing being moved to its first position subsequent to the activating signal being stored in the storage means. Thus, the activating signal is transmitted to the indicating means upon a subsequent operation of the apparatus by the housing being moved to its first position subsequent to an initial operation of the switch means.

Also in the preferred form, the control means comprises pulse generating means which generates first and second sets of pulses. There is a signal monitoring means responsive to the first set of pulses to monitor the condition signal periodically and provide an indicating signal when a predetermined signal condition is determined from said condition signal. The indicating means is responsive to the second set of pulses and the indicating signal from the signal monitoring means to cause indicating pulses to be transmitted through the indicating means. In the preferred form, the first set of pulses is at a lower frequency and the second set of pulses is at a higher frequency, whereby the indicating pulses are in a relatively higher frequency than the time periods at which the monitoring circuit is functional.

In accordance with another facet of the present invention, the apparatus is arranged to monitor temperature of milk from an animal within a range of a desired maximum measurement error value. The apparatus comprises a heat receiving portion that has a heat input surface portion positioned and arranged proximate to the passageway so as to be able to be in intimate heat exchange relationship with milk in the passageway. It also has a heat output surface portion and an intermediate heat conductive heat transfer portion having a predetermined thermal conductivity.

There is a temperature sensing device positioned proximate to said heat output surface portion so as to be in heat exchange relationship therewith and adapted to produce an output signal related to temperature sensed by the sensing means. There is also signal processing and indicating means responsive to the signal to produce an indicating output related to temperature as sensed by the temperature sensing device.

The apparatus is characterized in that it is adapted to operate in an ambient environment having a temperature range from a low ambient temperature to a high ambient temperature. The apparatus has a total heat sink to ambient through which heat is transferred to ambient.

The apparatus is further characterized in that it has two total heat transfer coefficients. There is a first coefficient related to heat transfer from the heat input surface portion to the temperature sensing device, and a second coefficient related to heat transfer from the temperature sensing device to the total heat sink.

The apparatus has an actual maximum measurement error value within the desired measurement error value, which is a maximum difference between actual milk temperature and temperature at the sensing device. The apparatus is constructed and arranged so that the ratio between the first and second heat transfer coefficients is at least as great as the ratio between the difference between the temperature of the sensing device at a temperature within the maximum temperature error and the low ambient temperature, and the desired maximum measurement error value. Thus, milk temperature can be reliably monitored within the desired measurement error.

In one embodiment, when the apparatus is an operating position relative to the milking device, the heat receiving portion is positioned so that its heat input surface portion defines with the wall means of the milking device a portion of the passageway through which milk flows in the milking device. More specifically, the heat receiving portion extends along a circumferential portion of said wall means that defines the passageway. Desirably the heat receiving portion has a substantially annular configuration extending substantially circumferentially around said passageway.

In the preferred form, the heat receiving portion has a sufficiently small thickness dimension so that when the heat receiving portion is subjected to an elevated temperature condition, the heat receiving portion is able to dissipate heat relatively rapidly and return to a normal operating level.

In another arrangement, the heat receiving portion comprises a probe adapted to extend through the wall means of the milking device. The probe has a tip positioned in the passageway, and the temperature sensing device is mounted in the tip. The apparatus further comprises electrically conductive leads extending from the temperature sensing device through the probe to the signal processing and indicating means. The electrically conductive leads are made sufficiently small so as to maintain the second total heat transfer coefficient within an acceptable level.

Desirably. the ratio between the first and second total heat coefficients is at least 200:1, more desirably at least 300:1, and in the preferred form at least about 350:1.

In the method of the present invention, a characteristic of the milk is monitored by applying the housing of the apparatus to a milking device, and then placing the milking device in its operational position to initiate operation of the apparatus. Desirably, the method is started by observing an indicating signal on the device to show that it is operational. The method can be practiced by observing the indicating means during a milking operation, and also by observing a delayed output signal observing the device at the conclusion of a milking cycle and prior to initiation of a second milking cycle.

Other features of the present invention will become apparent from the following detailed description.

BRIEF DESCRIPTION OF THE DRAWINGS

FIG. 1 is an isometric view of the claw of a conventional milking apparatus with the apparatus of the present invention attached thereto;

FIG. 2 is an isometric view of the apparatus of the present invention;

FIG. 3 is a sectional view taken through line 3—3 of FIG. 2;

DESCRIPTION OF THE PREFERRED EMBODIMENTS

Figure 4:
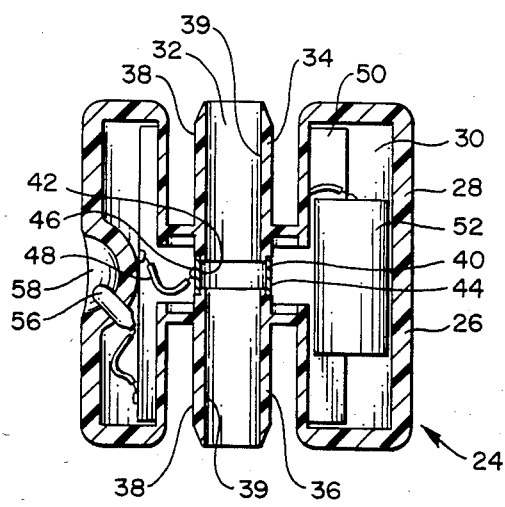
FIG. 4 is a longitudinal sectional view taken along line 4—4 of FIG. 3.

With reference to FIG. 1, there is shown a portion of a conventional milking apparatus, in the form of a claw 10, with its associated long milk tube 12 and long air hoses 14 The claw 10 comprises a manifold 16, four teat cups 18 and four short milk tubes 20 interconnecting the cups 18 with the manifold 16. In addition, there are four short air hoses 22, each leading from a related cup 18, and these air hoses 22 connect to the main air hoses 14.

The milking components 10-22 listed above are the same as, or similar to, those conventionally used in today's milking parlors. The cups 18 are connected to the teats of the cow's udder, and the operation of the suction applied through the hoses 14 is such that the milk is extracted from the cow's udder so as to flow through the cups 18 and tubes 20 to be collected in the manifold 16. The milk then flows from the manifold 16 through the main milk tube 12 to a collecting location.

The apparatus of the first embodiment of the present invention is generally designated 24. It comprises a generally cylindrical housing 26 which, in this embodiment, is spliced into one of the four milk tubes 20. The housing 26 is conveniently arranged in a generally cylindrical configuration, having a diameter of about 2 inches and an axial length also of approximately 2 inches. In the particular arrangement shown herein, this housing comprises a shell 28 which could conveniently be made into two sections from molded plastic. After the components of the device 24 are in place, the shell 28 can be filled with a suitable foam material, such as urethane foam, as indicated at 30.

The housing 26 is formed with a centralflow passage 32 extending along the axial center line of the cylindrical housing 26. This passage 32 is defined by upper and lower tubular sections 34 and 36, respectively, with the outer surfaces 38 of the sections 34 and 36 having a cylindrical configuration to receive sections of the milk tube 20 into which the temperature sensing device 24 is spliced. More specifically, one of the existing milk tubes 20 can be cut across its length, with the upper section being placed around the upper tubular section 34 so as to fit snuggly therearound, and the lower section of the tube 20 being placed snuggly around the lower tubular section 36. As will be discussed more fully hereinafter, the apparatus 24 can remain in its position spliced into the tube 20 indefinitely.

Located between the upper and lower tube sections 34 and 36 is a heat receiving ring 40. This ring 40 has a generally cylindrical configuration, and its inner surface 42 has a diameter nearly the same as the diameter of the inner surfaces 39 of the upper and lower tubular sections 34 and 36. Thus, this inner ring surface 42 forms a middle portion of the aforementioned through passage 32. This ring 40 is made of a material having a relatively high thermal conductivity, and in the preferred configuration, is made of stainless steel. The sizing, configuration, arrangement, and thermal conductivity of the ring 40, relative to the rest of the device 24 are critical in the present invention, and these will be discussed in more detail later herein.

Positioned against the radially outward surface 44 of the ring 40 is a thermistor element 46. The thermistor 46 is in turn connected by leads 48 to the circuitry contained in a flexible circuit board 50. This circuit board 50 is conveniently sized and arranged to fit in a generally curved configuration within the housing 26.

Also positioned within the housing 26 is a battery 52, which is the power source for the device 24. As shown herein, the outer wall 54 of the housing 26 protrudes outwardly to a moderate extent in the location of the battery 52. Also, there is an alarm or signal light 56 positioned at the sidewall 54, with the sidewall 54 being recessed moderately at 58 to accommodate the light 56, so that the light 56 can remain within the confines of the geometry of the cylinder defined by the housing 26.

Before describing the temperature sensing device 24 in more detail, it may be helpful if, at this point, the general mode of operation of the present invention is disclosed.

As indicated above, the device 24 is spliced into one of the four milk tubes 20, and it can remain in that position indefinitely. In effect, it becomes part of the claw 10. In other words, when the claw 10 is removed from the cow and hung up, the device 24 remains connected to the claw, ready for use during the next milking operation.

In use, as the milk flows through the tubes 20, the milk comes in heat exchange contact with the heat receiving ring 40, so as to quickly raise the temperature of the ring 40 to that of the milk. The temperature is sensed by the thermistor element 46, and the circuitry 50 is arranged so that an alarm signal is directed to the light 56 (more precisely, an LED 56) when temperature above a certain level is sensed by the thermistor 46. The alarm signal emitted by the LED 56 is in the form of a blinking light.

There are two broad aspects of the present invention which will be described in more detail hereinafter. One is the arrangement of the circuitry to make the operation of the device 24 totally automatic, without any need to manipulate an on-off switch, without any adjusting of a control element, etc. Also this circuitry is arranged to provide an indicating signal to inform the user that the device 24 is operational, and it is arranged so as to conveniently display an alarm signal at the appropriate times, not only during use, but at a later time prior to subsequent use of the device. Further, the control circuitry is arranged so that it draws substantially no power during periods of non-use, thus making it possible to have the unit be totally selfcontained and remain operational during normal use for a number of years.

The other facet or aspect of the present invention which is considered significant is the arrangement of the components relative to the somewhat subtle and previously unrecognized heat transfer relationships of the components. This enables the device 24 to be used reliably and without need for adjustments from time to time, regardless of the operating conditions (i.e. whether it is used in near freezing weather or at high temperatures that could occur on very warm days).

With regard to the operation of the control circuitry, before describing the circuitry in detail, it may be helpful to disclose generally the sort of signals generated. The device 24 is provided with a tilt switch (shown in FIG. 8 at 60) which closes (thus making device 24 operational) only when the device 24 is placed in an upright position as shown in FIG. 1. In situations where the claw 10 is not in use so that it is hung on a suitable hanger or hook, the cups 18 normally hang downwardly so that the device 24 is inverted. In such a position, the tilt switch 60 opens so as to stop any significant draw of current from the battery 52.

To indicate further the operation of the control circuitry, let it be assumed that in the normal course of operation, the operator takes the claw 10 in hand and moves the device 24 to an upright position so that he can observe the light 56 briefly. The control circuitry is so arranged that as soon as the tilt switch 60 is initially closed (by moving the device 24 to its upright position), there is a brief pulse which causes the light 56 to blink once to indicate that the device 24 is functional. When the claw 10 is attached to the cow so that milk begins to flow through the tubes 20, the control circuitry reads the temperature for a brief moment at regular intervals (at eight second intervals in the preferred embodiment herein). If a temperature above a certain level is detected even for that brief instant, the control circuitry continues to direct a series of pulses to the light 56 at regular short intervals (at one second intervals in this embodiment). This alarm signal (i.e. the blinking of the light 56 at one second intervals) continues until the cup 18 is released from the cow's teat and inverted. (In many milking machines, the release of the cup 18 is automatic at the completion of the milking cycle, this being triggered by the suction apparatus sensing that it is not extracting milk from the cow at a minimum flow level.)

Let it be assumed that the operator, upon initially observing that the device 24 was operational by the single "I am functional" blink of the device 24, places the claw 10 in its milking position as shown in FIG. 1, but then moves to another milking station so that he is not able to observe the device 24. Let it be assumed that the temperature of the milk is high enough to initiate the alarm circuit so that the light 56 begins blinking. However, at the completion of the milking cycle, the cup 18 falls from the cow so that the device 24 is inverted, thus opening the tilt switch 60 and causing the device 24 to become non-operational. This would stop the light 56 from blinking which had gone unobserved by the operator. However, the device 24 is provided with a memory so that when the device 24 is again moved to its upright position for the next milking, the light 56 again begins blinking for a suitable interval (in the present embodiment, for about four seconds) to warn the operator that during the immediately previous milking, a temperature over the threshhold level was detected. At the conclusion of that four second interval of blinking, the device 24 goes back to its original mode of operation, such as described above.

Figure 8:
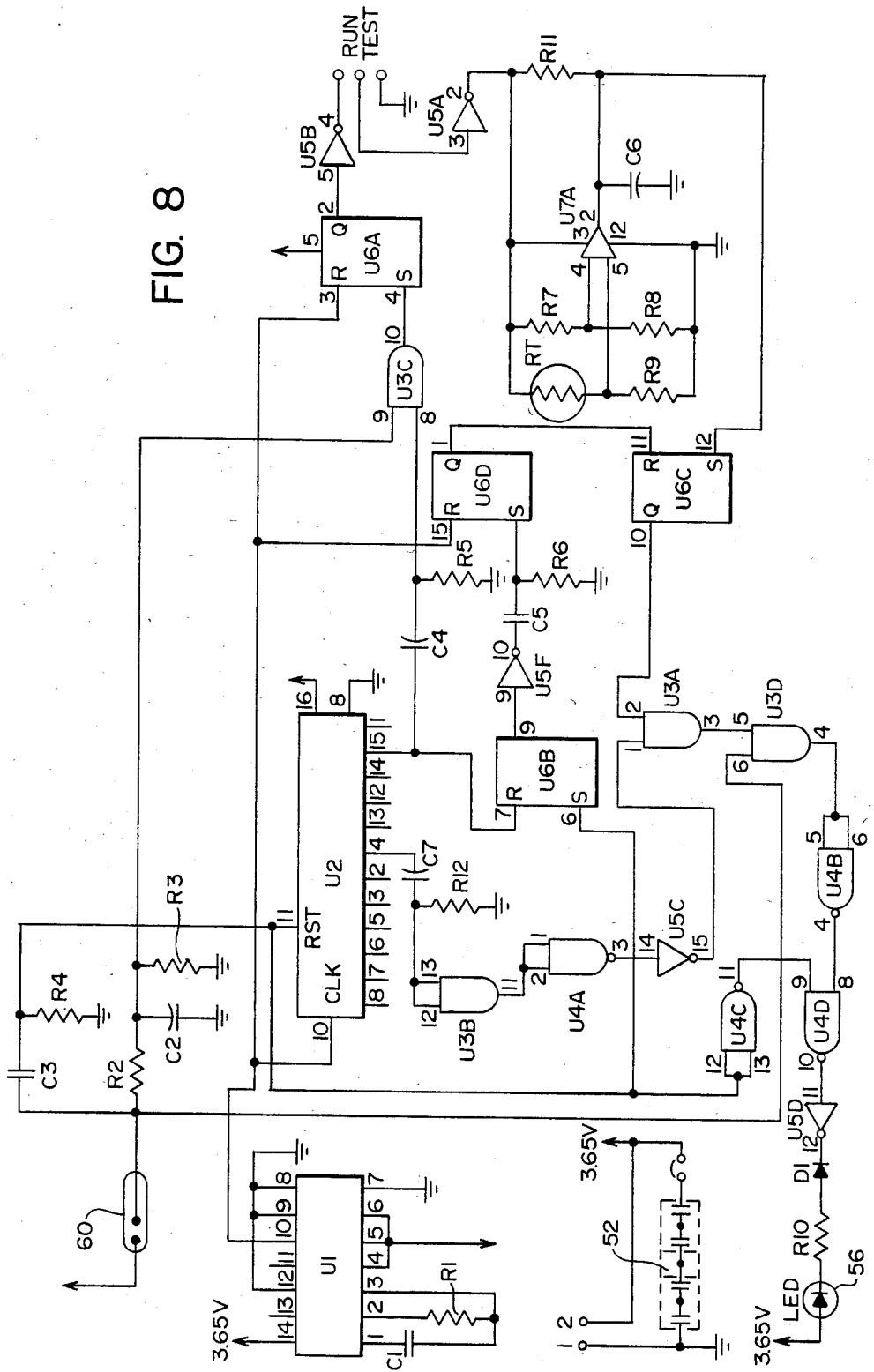
FIG. 8 is a schematic view illustrating the circuitry of the present invention.

The circuitry for the device 24 is illustrated in FIG. 8. The battery 52 is a 3.65 volt lithium cell with a capacity of 850 mA-hr. In the present arrangement, this should be sufficient to run the device 24 for several years under circumstances where it is not registering high temperatures in the cows.

There is an ultra low power oscillator U1, having an associated resistor R1 and capacitor C1, which are set for the oscillating frequency to be 100 Hz. The output from terminal 10 of the oscillator U1 is transmitted to the clock input of the divider U2. The function of the divider U2 is to provide two sets of timing pulses of known duration.

Operation of the divider U2 is commenced when the device 24 is moved to the upright position so as to close the tilt switch 60 so as to transmit voltage to the reset input at 11 of the divider U2. The length of the reset pulse is determined by resistor R4 and capacitor C3. This reset pulse is also coupled to the display LED 56 via inverter U4C to the gate U4d to provide the "I'm alive" blink in the LED 56. In the present application, the gate U4D is a positive logic NAND gate which, in the present application, is being used as a negative logic gate to look for a low signal for either input terminal 9 or 8, which will in turn produce a high level output. The inverter U5D transmits this same output at a higher power level to cause the LED 56 to blink.

The timing pulses at the pin 4 of the divider U2 are square waves with a period of approximately 1 second. The resistor R12 serves to reduce the duty cycle of these pulses and provides pulses with a duration of about 100 milliseconds repeated at the 1 second rate determined by the divider U2. These pulses are passed through the AND gate U3B, thence through the NAND gate U4A (which is used as an inverter) and thence through the inverter U5C, the output of which goes to one input of the AND gate U3A. As will be described hereinafter, when the other input of the AND gate U3A is activated when a high temperature condition is sensed, it will then begin transmitting the 1 second alarm pulses to the LED 56, provided the switch 60 is closed.

The latch U6B is a memory element that is set to a high condition when it receives a pulse at its input S and it goes to a low condition when it receives a pulse at its reset input R. (This set pulse is generated by tipping the device 24 upright so as to close the switch 60.) Four seconds after the latch U6B is set, it is then reset by a pulse from the pin 14 of the divider U2. (As will become apparent hereinafter, this 4 second interval provided by the latch U6B is the interval during which the LED 56 blinks for 4 seconds to indicate that the immediately preceeding use of the device 24 indicated a high temperature.)

The 4 second pulse from the latch U6B is inverted by the inverter U5F and transmitted to capacitor C5, resistor R6 and to the latch U6D, where it becomes a delayed reset pulse present at the Q output of U6D. This reset pulse has a duration of only about 1/100 second.

The AND gate U3C has one input connected to the tilt switch 60 and a second input connected to the output 14 of the divider U2. When the tilt switch 60 is closed, the AND gate U3C provides a pulse to the latch U6A every 8 seconds. The latch U6A shortens its pulse to exactly 10 milliseconds. This 10 millisecond pulse which occurs every 8 seconds is used to power the temperature measuring circuit. The temperature measuring circuit would consume about 45 mW if power is used continuously. Therefore, the pulse power configuration is used to extend battery life. This latch U6A continues to generate the pulses at 8 second intervals as long as the switch 60 remains closed (i.e. the device 24 remains upright).

The temperature measuring circuit consists of the comparator U7A and a bridge circuit made up of the resistors R7, R8, R9 and RT (resistor RT being the temperature sensitive resistor in the thermistor element 46).

For temperatures above or below the trigger point, the bridge becomes unbalanced. The comparator U7A provides a signal that is either logic high or low depending upon the polarity of the imbalance of the bridge. Since the bridge is unbalanced by the action of temperature on the thermistor 46, the signal present at the output of the comparator U7A indicates a temperature above or below the trigger point. The resistor R9 is selected to be equal to the resistance of the thermistor 46 at the trigger temperature. The output is logic low for temperatures lower than the trigger temperature and changes to logic high for temperatures greater than the trigger temperature.

The state of the temperature measuring circuit is stored in the memory of the register U6C. It stays in the register U6E until it is cleared out by the delay reset pulse from the latch U6D.

The AND gate U3A will pass the short pulses at a frequency of one every one second if the memory register U6C is in a logic high state indicating a temperature higher than the trigger temperature. These 1 Hz short pulses are passed through the AND gate U3D if the unit 24 is in the upright position. Thus, the LED 56 blinks at a 1 Hz rate if the temperature is above the trigger point and the unit 24 is upright.

If the unit 24 falls over, the blinking of the LED 56 will cease, thus conserving power. However, the memory register U6C is not reset until 4 seconds after the unit is returned to the upright position. If the temperature were hotter than the trigger point before the unit fell, the LED 56 will blink for 4 seconds after the unit is brought to the upright position. Thus, as indicated earlier, in those circumstances where the device 24 is blinking while it is attached to the cow so as to register a high temperature, if the device 24 then falls from the cow so as to open the switch 60, at such time as it is returned to the upright position to close the switch 60, the output from the memory register U6C will continue to cause the LED 56 to blink, until such time as it receives the pulse from the latch U6D to terminate the output at Q of U6C.

The other major aspect of the present invention is the arrangement of the components relative to the heat exchange relationships that exist. As indicated previously, the temperature monitoring device must operate in a milking parlor environment which has rather dramatic temperature extremes in the work areas, in that ambient temperature may be expected to fluctate anywhere from 32° F. to 100° F. Of greater concern is the effect of temperatures at the lower end of the range.

In the present invention, the device 24 is adapted to be placed at the location of the tube 20 just below the cup 18. In that position, the elapsed time period during which the milk leaves the cow's udder and travels through the passage 32 of the device 24 is sufficiently brief so that with full flow the temperature of the milk changes very little by the time it reaches the device 24. Thus, the temperature drop of the milk is not in the present invention any real source of error, even when the ambient temperature is as low as 32° F. However, while the temperature sensor location is an important consideration, it has been discovered by the applicant that this is by no means the only critical factor in obtaining an accurate temperature reading. Rather, certain heat emchange relationships associated with the temperature sensing element have been discovered to be a critical factor. This will be discussed more fully below.

For purposes of analysis, let us propose a somewhat idealized model of a temperature sensing apparatus. In this model we have essentially five elements, namely: the heat collecting element 70, the temperature monitoring element 72, the signal transmitting leads 74, the housing and filler material 76, and finally the heat sink to ambient 78. To relate this model to the first embodiment 24, the heat collecting element 70 corresponds to the heat receiving ring 40. The temperature measuring element 72 corresponds to the thermistor element 46; the signal transmitting leads 74 correspond to the leads 48; and the housing and filler material 76 correspond to the housing 26 made up of the shell 28 and foam 30. The heat sink to ambient 78 comprises the control circuitry 50, the housing 26, and in general the components of the device 24 which are able to draw heat and transmit the heat to the ambient atmosphere.

To return now to the model of FIG. 8, the following definitions apply:

A1: The heat receiving surface area of the heat collecting element 70 which is in contact with the milk.

A2: The heat transmitting surface area of the heat collecting element 70 which is in contact with the temperature measuring element 72.

A3: The heat receiving surface area of the signal transmitting leads 74.

A4: The heat transmitting surface are of the signal transmitting leads 74.

A5: The heat receiving area of the housing and filler material 76.

A6: The heat transmitting area of the housing and filler material 76.

L1: The distance between the heat receiving surface area A1 of the heat collecting element 70 and the heat transmitting surface A2 thereof.

L2: The distance between the heat receiving areas A3 and A5 of the signal transmitting leads 74 and the housing and filler material 76, respectively, and the heat transmitting surfaces A4 and A5 thereof.

K1: The thermal conductivity of the heat collecting element 70.

K2: The thermal conductivity of the signal transmitting leads 74.

K3: The thermal conductivity of the housing and filler material 76.

$T_m$: The temperature of the milk.

$T_t$: Temperature of the thermistor (i.e. the temperature measuring element).

$T_a$: Temperature of the ambient atmosphere.

$\Delta t$: The error in the temperature measurement.

Q1: Equals the heat transmitted from the milk to the temperature sensing element.

Q2: The transfer of heat from the temperature measuring elexent to the heat sink to ambient.

For purposes of analysis, it is assumed that area A1 equals area A2, and that the sum of areas A3 and A5 are equal to the sum of areas A4 and A6, and that each of these sums is equal to the area A1 and also equal to the area A2. It is also assumed that the areas A1 and A2, as well as the sum of the areas A3 and A5 and also the sum of the areas A4 and A6 are each a perfect square measured 0.1 inch on each side. Further it is assumed that the heat collecting element 70 is uniform with respect to its cross-sectional area, that it is made of stainless steel, and that its thickness dimension (L1) is 0.01 inch. With regard to the temperature measuring element 72, assume that its thickness dimension is zero, or stated another way, that its resistance to transfer of heat from surface area A2 to surface area A3 is zero. With regard to the signal transmitting lead 74 and the housing and filler material 76, it is assumed that these have a uniform cross-section. We have further assumed that the signal transmitting leads 74 together have the cross-sectional configuration of a single square having an edge dimension of 0.01 inch. The surrounding housing and filler material 76 is assumed to fill the rest of the cross-sectional area, and it likewise has a square configuration, but with an edge dimension of 0.1 inch. Thus, the cross-sectional area of the leads 74 is 0.0001 inch, and the cross-sectional area of the housing and filler material 76 is 0.0099 inch. The assumption is made that the leads 74 are made of copper, while the housing and filler material is made of urethane foam. Further assumed is that the distance from area A3 to area A4 (L2) is 0.5 inch.

The thermal conductivity of the materials noted above, measured in Btu/hr/sq. ft. are given as follows:

| | |
|---|---|
| Copper | 226.00 |
| Stainless Steel | 11.70 |
| Urethane Foam | 0.30 |

In a stable state condition, the heat transmitted from the milk at surface A1 to the temperature measuring element at surface A2 equals the rate at which heat is extracted at the surfaces A3 and A5 and delivered to the surface A4 and A6. The rate of heat transfer is directly proportional to the thermal conductivity of the material multiplied by the cross-sectional area of the material in the heat transfer path and further multiplied by the temperature differential existing between the heat input and heat output surfaces. The rate of heat transfer is further inversely proportional to the length dimension between the two heat transfer surfaces. Thus, the formula representing such a stable condition would be as follows:

$$\frac{K_1(A_1 + A_2)(T_m - T_t)}{2L_2} =$$

$$\frac{K_2(T_t - T_a)(A_3 + A_5)}{2L_2} + \frac{K_3(T_t - T_a)(A_4 + A_6)}{2L_2}$$

If we insert the appropriate numerical values in accordance with our assumptions above, we have the following:

$$\frac{11.7(T_m - T_t)(0.01 + 0.01)}{2(0.01)} =$$

$$\frac{226(T_t - T_a)(0.0001 + 0.0001)}{2(0.5)} +$$

$$\frac{0.03(T_t - T_a)(0.0099 + 0.0099)}{2(0.5)}$$

$11.7(T_m - T_t) = 0.0446(T_t - T_a) = 0.00594(T_t - T_a)$ $11.7(T_m - T_t) = 0.05054(T_t - T_a)$

-continued $$\frac{T_m - T_l}{T_l - T_a} = \frac{1}{231}.$$

If we calculate further, we find the ratio of the temperature differential across the heat collecting element 70 to the temperature differential across the housing and filler material 76 and lead 74 to be 1:231. If we further assume the temperature of the cow's milk to be 100° F. and ambient temperature to be at a low of 32° F., the total temperature differential is 68° F. By applying the above ratio, we can can calculate the temperature differential across the heat collecting element 70 to be about 0.3° F. This differential in the following analysis will be called the "increment of error", or for short "$\Delta t$".

In reviewing the formulas given above, it also becomes apparent that, at least for the idealized model noted above, by far the greatest factor (by a factor of over 10) in contributing to the error is the copper leads connected to the temperature measuring element 72.

With regard to the error which would be acceptable in this type of temperature monitoring instrument, first, we have to recognize that the milk temperature in an average cow is about 100.5° F. However, as with humans, the normal temperature of a healthy cow will vary somewhat, and could even be as high as 101.5° F. A fever level would occur approximately at 103° F. Accordingly, to have a reasonably reliable monitoring instrument, the margin of error should certainly be no greater than 0.5° F., and more desirably would be within 0.2° F.

Figure 9:
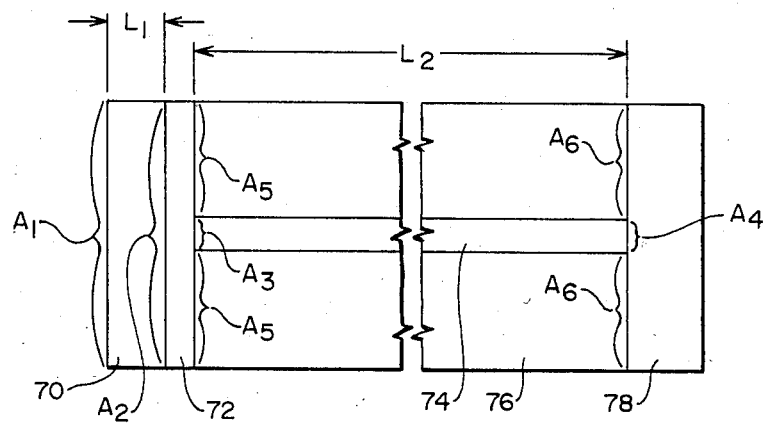
FIG. 9 is a highly schematic view of a heat transfer model for analysis of the heat transfer aspects of the present invention.

In the idealized model of FIG. 9, and with the numerical assumptions made relative to that model, we arrived at a $\Delta_t$ (i.e. an error factor) of about 0.3° F.

For purposes of further discussion, we can use the term "total thermal conductivity coefficient" to describe the rate of heat transfer for a given temperature differential from the heat receiving to the heat transmitting surface. With the numerical values in the idealized example given above, the thermal conductivity coefficient of the heat collecting element 70 was approximately 231 times as great as the total thermal conductivity coefficient of the transmitting leads and filler material. This falls somewhat short of the desired minimum ratio, since the increment of error was about 0.3° F. Desirably, the total heat transfer coefficient of the heat transferred into the temperature measuring element would be at least approximately 350 times that of the total heat transfer coefficient of the material extracting heat from the temperature measuring element. Within the broader scope of the present invention, possibly a ratio of 300:1 could be acceptable, and even as low as 200:1. However, while in some situations that may be considered acceptable, it is certainly not the desired ratio.

One of the ways to optimize the ratio of the total heat transfer coefficients is to improve the heat collecting and transferability of the heat collecting element 70, which in the first embodiment corresponds to the heat collecting ring 40. In the first embodiment shown in FIGS. 1–4, this was done by forming this element 40 in the configuration of a ring which extends totally around the circumference of the passageway 32. Further, the ring 40 was made relatively thin (0.01 inch). The ring 40 is made of stainless steel, which admittedly is not the best conductor among the various metalic conductors. However, from a standpoint of sanitation, stainless steel is quite desirable for use in a milking operation, and the thermal conductivity level of stainless steel is sufficiently high to serve satisfactorily in the present invention.

While in the idealized model, we have considered the temperature measuring element 72 (which in the first embodiment corresponds to the termistor 46) to have no effect in heat transfer, in a real device, it obviously does have some effect. It is necessary to encapsulate the electrical resistor in the thermistor 46, with a thin coating of an electrically insulating material so that the thermistor 46 would not short out when it is placed against the stainless steel ring 40. However, this encapsulating material for the termistor can be made of a high heat conductive electrically insulating material, and also could be made quite thin so as to minimize its insulating effect.

The next step to reduce the error would be to minimize the thermal conductivity characteristics of the transmitting leads 74, which in the present embodiment of FIGS. 1–4 are the leads 48. The obvious way of doing this is to reduce the cross-sectional area of the leads 48, and this can be done within limits. In the numerical assumptions of the example given above relative to the idealized model, the leads were assumed to have a total cross-sectional area of about 0.0001 inch which would be a square cross-section having 0.01 inch on each side. In a standard thermistor which is commercially available, the two leads actually may be about 0.008 inch, and leads of this diameter can be used quite conveniently, in that they are reasonably easy to handle and are not particularly fragile. However, it is possible to reduce the leads to smaller diameters. In the first embodiment, it was found that the 0.008 diameter leads were satisfactory, and this appromimates the cross-sectional area of the leads 74 in the model of FIG. 9.

With the temperature mounting device 24 arranged with the components as recited above, it has been found that the total heat transfer coefficients into and from the thermistor 48 is greater than 350:1, thus leaving a quite acceptably low margin of error in the temperature measurement.

A further consideration relative to the monitoring device 24 is that the milk from the cow will not at all times totally fill the passageway 32. In those circumstances, the milk will be in contact with only part of the ring 40. However, it has been found with this arrangement that even under these circumstances, temperature readings within acceptable margins of error can be achieved.

A further consideration is that in some milking units, there is an automatic back washing operation between each milking cycle. In this back washing, hot water is flushed back through the milking device itself, and this hot water could be as high as 160° F. This would, of course, raise the temperature of the ring 40 and of the thermistor 46 well above the alarm level. Thus, there would be the possibility of the device 24 giving false readings when it is next applied to the cow for the following milking operation. However, it has been found that by making the ring 40 quite thin (e.g. about 0.01 inch), the rate at which the ring 40 can dissipate its heat to air within the tube passageway 32 and into the device 24 is sufficiently fast so that such false readings would not result.

Figure 5:
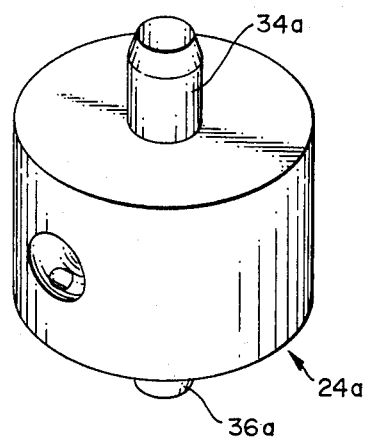
FIG. 5 is an isometric view of a modified form of the housing of the embodiment shown in FIGS. 1-4.

A slightly modified form of the first embodiment is shown in FIG. 5. Instead of making the tubular members 34 and 36 recessed, these two members are made to extend above and below the upper and lower surfaces of the device 24. To distinguish the modification shown in FIG. 5, the overall device is indicated at 24a, and the upper and lower tubes are indicated at 34a and 36a.

Figure 6:
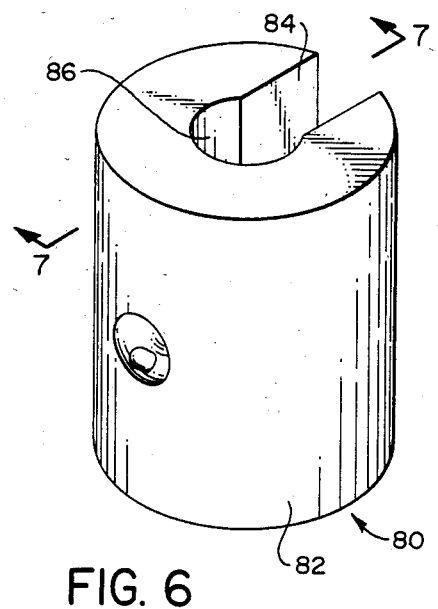
FIG. 6 is an isometric view of a second embodiment of the present invention.

A second embodiment is illustrated in FIGS. 6. 7 and 10. In this second embodiment, generally designated 80, there is a generally cylindrical housing 82 having a radially extending through slot 84 that extends the entire axial length of the housing 82. The center of the housing 82 is formed with a passageway 86 having a generally circular configuration, with the passageway 86 connecting to the slot 84. The slot 84 has a diameter moderately smaller than that of the milk tube 20, and the passageway 86 has a diameter substantially the same as the outside diameter of the tube 20. Thus, the tube 20 can be squeezed through the slot 84 and fit snuggly in the passageway 86.

There is a probe 88 which extends from the passageway wall 86 radially inwardly toward the slot 84. This probe 88 has a generally cylindrical shank 90, and a tip 92. The tip 92 has a generally conical configuration, with an outer point 94 and an expanded base 96. The diameter of the base 96 is slightly larger than the shank 90.

A thermistor 98 is encapsulated in the tip 92, and there are two leads 100 embedded or encapsulated in the shank 90, these leads 100 connecting to the termistor 98. The control circuitry and alarm light of the present invention are substantially the same as in the previous embodiment, so these are given numerical designations of 102 (for the circuitry) and 104 (for the light), but no detailed description is given.

In operation, a small hole is formed in the tube 20 and the tube 20 is pushed into the slot 84 and pressed against the tip 92. The tip 92 is pushed through the hole in the wall of the tube 20, and the expanded base 96 of the tip 92 holds the tip 92 in place against the inside surface of the wall of the tube 20.

Figure 10:
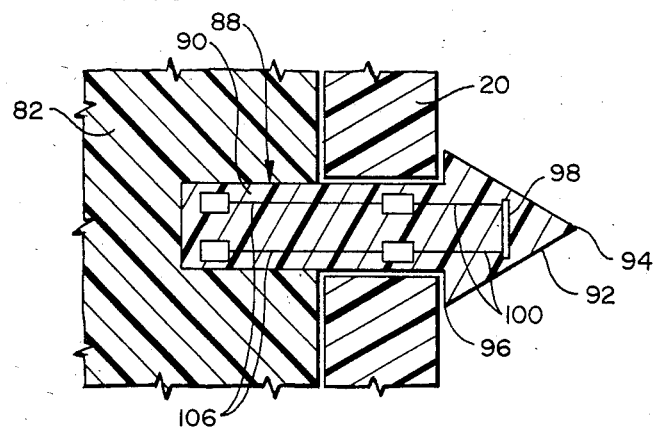
FIG. 10 is an enlarged view of the sensing element of the second embodiment and the components in proximity thereto.

The probe 88 is shown to a somewhat enlarged scale in a sectional view of FIG. 10. As a practical matter, it is necessary to provide the tip 92 with a sufficiently large size so that it is rugged enough to withstand normal use. In other words, with the tip 92 mounted in the wall of the tube 20, it will have to withstand a certain amount of force during the jostling of normal use. Thus, it is necessary to have a minimum amount of material in the tip 92 encapsulating the thermistor 98, and this will to some degree diminish the effectiveness of heat transfer from the milk into the thermistor 98. This can be alleviated to a large extent by optimizing the location of the thermistor 98 and also making the material of the tip 92 with a high thermal conductivity.

Figure 7:
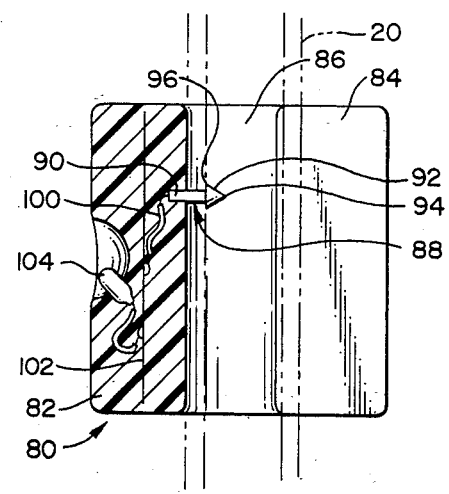
FIG. 7 is a sectional view taken along line 7—7 of FIG. 6.

Even so, during the experimental and developmental work of the embodiment shown in FIGS. 6, 7 and 10, it was found that under extreme operating conditions (i.e. quite low ambient temperature), the margin of error in temperature measurement was unacceptably high. It was found that this could be alleviated by providing portions of the leads 100 with two lead portions 106 of very small diameter. It was found that if these leads 106 were made of gold of about 0.001 inch thickness. the overall heat transfer coefficient could be kept sufficiently small so that the thermistor 98 would give a reading of relatively high accuracy.

It is to be understood that the embodiments are shown in detail to illustrate preferred forms of the invention and that various modifications could be made within the broader aspects of the present invention.

I claim:
1. An apparatus to monitor a characteristic of milk that is taken from an animal, said apparatus being adapted to be used in conjunction with a milking device that extracts the milk from the animal, said apparatus comprising:
  (a) a hosuing adapted to be mounted relative to shid milking device so as to have a first operating position where the housing has a first postitional orientation when the milking device is in use, and a second non-operating position where the housing has a second positional orientation when the milking device is not in use;
  (b) a sensing means adapted to sense a predetermined condition of said characteristic of the milk and transmit a condition signal related to said condition;
  (c) indicating means to provide an indicating output of the condition of the characteristic of the milk;
  (d) a control means to receive said condition signal and to cause said indicating means to provide its output in accordance with said condition signal;
  (e) switch means responsive to the positional orientation of said housing to cause said apparatus to be operational when said housing is in its first position and and to cause said apparatus to be non-operational when said housing is in its second position;
  (f) said control means comprising circuit means to generate an activating signal at a first time and further comprising signal storing means to store said activating signal so as to delay transmittal of the same, and to transmit said activating signal to said indicating means at a subsequent time, said storage means being responsive to said switch means being activated by said housing being moved to its first position subsequent to said activating signal being stored in said storage means, whereby said activating signal is transmitted to said activating means upon a subsequent operation of said apparatus by said housing being moved to its first position subsequent to an initial operation of said switch means.

2. The apparatus as recited in claim 1, further comprising circuit means to give an operational indicating signal in response to the switch means causing said apparatus to become operational.

3. The apparatus as recited in claim 1, wherein said control means comprises circuit means to give an indicating signal for the indicating means at the time that said sensing means is sensing said condition of said milk.

4. The apparatus as recited in claim 1, wherein said control means comprises:
  (a) first circuit means to give an operational indicating signal in response to the switch means causing said apparatus to become operational;
  (b) pulse generating means which generates a first and a second set of pulses;
  (c) signal monitoring means responsive to said first set of pulses to monitor the condition signal periodically and provide an indicating signal when a predetermined signal condition is determined from said condition signal;
  (d) said indicating means being responsive to said second set of pulses and the indicating signal from the signal monitoring means to cause the indicating pulses to be transmitted through said indicating means;

(e) said signal storing means being responsive to said switch means being activated by said housing being moved to its first position.

5. The apparatus as recited in claim 1, wherein said housing is arranged to be mounted to a tube that receives milk from the animal and transmits the milk to a collector, where said tube has an upright operating position, and a non-upright non-operating position.

6. The apparatus as recited in claim 5, wherein said housing is provided with a lateral slot to receive said tube so that said housing can be mounted to said tube through said slot.

7. The apparatus as recited in claim 5, wherein said housing has first and second tube connecting means adapted to be connected to first and second connecting portions of said tube.

8. The apparatus as recited in claim 1, wherein said control means comprises pulse generating means which generates a first and a second set of pulses, signal monitoring means responsive to said first set of pulses to monitor the condition signal periodically and provide an indicating signal when a predetermined signal condition is determined from said condition signal, said indicating means being responsive to said second set of pulses and the indicating signal from the signal monitoring means to cause indicating pulses to be transmitted through said indicating means.

9. The apparatus as recited in claim 8, wherein said first set of pulses is at a lower frequency and said second set of pulses is at a higher frequency, whereby said indicating pulses are at a relatively higher frequency than time periods at which said monitoring circuit is functional.

10. An apparatus to monitor temperature of milk from an animal within a range of a desired maximum measurement error value, said apparatus being adapted to be used in conjunction with a milking device which has at least one passageway member having a wall means defining a passageway through which milk from the animal flows, said apparatus comprising:

(a) a heat receiving portion having a heat input surface portion positioned and arranged proximate to said passageway so as to be able to be in intimate heat exchange relationship with milk in said passageway, a heat output surface portion, and an intermediate heat conductive heat transfer portion having a predetermined thermal conductivity;

(b) a temperature sensing device positioned promimate to said heat output surface portion so as to be in heat exchange relationship therewith and adapted to produce an output signal related to temperature sensed by said sensing means;

(c) signal processing and indicating means responsive to said signal to produce an indicating output related to temperature as sensed by said temperature sensing device;

(d) said apparatus being characterized in that it is adapted to operate in an ambient environment having a temperature range from a low ambient temperature to a high ambient temperature, said apparatus having a total heat sink to ambient through which heat is transferred to ambient;

(e) said apparatus being further characterized in that it has two total heat transfer coefficients, a first coefficient related to heat transfer from said heat input surface portion to said temperature sensing device, and a second coefficient related to heat transfer from said temperature sensing device to said total heat sink;

(f) said apparatus having an actual maximum measurement error value within said desired measurement error value, which is a maximum difference between actual milk temperature and temperature at said sensing device, the apparatus being constructed and arranged so that the ratio between the first and second heat transfer coefficients is at least as great as the ratio between the difference between the temperature of the sensing device at a temperature within said maximum temperature error and the low ambient temperature, and the desired maximum measurement error value;

whereby milk temperature can be reliably monitored within the desired maximum measurement error.

11. The apparatus as recited in claim 10, wherein said heat receiving portion comprises a probe adapted to extend through said wall means fo the milking device, with said probe having a tip adapted to be positioned in said passageway, said temperature sensing device being mounted in said tip, said apparatus further comprising electrically conductive leads extending from said temperature sensing device through said probe to said signal processing and indicating means, said electrially conductive leads being made sufficiently small so as to maintain the second total heat transfer coefficient within an accpetable level.

12. The apparatus as recited in claim 10, wherein with said apparatus in an operating position relative to said milking device, said heat receiving portion is positioned so that its heat input surface portion defines with said wall means a portion of the passageway through which milk flows in the milking device.

13. The apparatus as recited in claim 12, wherein said heat receiving portion extends along a circumferential portion of said wall means that defines said passageway.

14. The apparatus as recited in claim 13, wherein said heat output surface portion of the heat receiving portion is positioned away from said passageway, and said temperature sensing device is connected by electrically conductive leads to said signal processing and indicating means, said signal processing and indicating means comprising circuit board means spaced from said temperature sensing device.

15. The apparatus as recited in claim 13, wherein said heat receiving portion has a substantially annular configuration extending substantially circumferentially around said passageway.

16. The apparatus as recited in claim 15, wherein said heat receiving portion has a sufficiently small thickness dimension so that when said heat receiving portion is subjected to an elevated temperature condition, said heat receiving portion is able to dissipate heat relatively rapidly and return to a normal operating level.

17. The apparatus as recited in claim 10, wherein the ratio between the first and second total heat transfer coefficients is at least 200:1.

18. The apparatus as recited in claim 17, wherein the ratio between the first and second total heat transfer coefficients is at least approximately 300:1.

19. The apparatus as recited in claim 18, wherein the ratio between said first and second total heat transfer coefficients is at least about 350:1.

20. A method of monitoring a characteristic of milk that is taken from an animal, said method comprising providing a monitoring apparatus comprising:

(a) housing adapted be mounted relative to said milking device so as to have a first operating position where the housing has a first positional orientation when the milking device is in use, and a second non-operating position where the housing has a second positional orientation when the milking device is not in use;

(b) a sensing means adapted to sense a predetermined condition of said characteristic of the milk and transmit a condition signal related to said condition;

(c) indicating means to provide an indicating output of the condition of the characteristic of the milk;

(d) a control means to receive said condition signal and to cause said indicating means to provide its output in accordance with said condition signal;

(e) switch means responsive to the positional orientation of said housing to cause said apparatus to be operational when said housing is in its first position and the cause said apparatus to be non-operational when said housing is in its second position;

(f) said control means comprising circuit means to generate an activating signal at a first time and further comprising signal storing means to store said activating signal so as to delay transmittal of the same, and to transmit said activating signal to said indicating means at a subsequent time, said storage means being responsive to said switch means being activated by said housing being moved to its first position subsequent to said activating signal being stored in said storage means, whereby said activating signal is transmitted to said activating means upon a subsequent operation of said apparatus by said housing being moved to its first position subsequent to an initial operation of said switch means;

said method further comprising mounting said apparatus to a component of a milking machine that during operation has an upright position and during non-operation has a non-upright position, then placing said milking device in an operating position so as to extract milk from the animal, and then removing the milking device from the animal and then placing the apparatus in an operating position on another animal, said method further comprising observing the indicating means either when the apparatus is in said operating position relative to the animal or subsequently when the apparatus is returned to said first positional orientation after milking of the animal and when placing the apparatus on the other animal to determine if there is an output indicating a predetermined condition of the characteristic of the milk.

21. The method as recited in claim 20, wherein said apparatus comprises circuit means to give an operational indicating signal in response to the switch means causing said apparatus to become operational, said method comprising observing said operational signal at initiation of a milking cycle.

22. The method as recited in claim 20, further comprising mounting said housing to a tube that receives milk from the animal and transmits the milk to a collector, where said tube has an upright operating position, and a non-upright non-operating position.

23. The method as recited in claim 22, wherein said housing is provided with a lateral slot to receive said tube, and said housing is mounted to said tube through said slot.

24. The method as recited in claim 22, wherein said housing has first and second tube connecting means, and said housing is connected to first and second connecting portions of said tube.

* * * * *